United States Patent [19]

Green et al.

[11] 4,182,749
[45] Jan. 8, 1980

[54] CHEMICAL SYNTHESIS APPARATUS AND METHOD

[75] Inventors: Malcolm L. H. Green, Oxford; Vivian J. Hammond, London, both of England

[73] Assignee: G. V. Planer Limited, Sunbury on Thames, England

[21] Appl. No.: 862,514

[22] Filed: Dec. 20, 1977

[30] Foreign Application Priority Data

Dec. 23, 1976 [GB] United Kingdom ............... 53705/76

[51] Int. Cl.² ............................................... B01J 1/00
[52] U.S. Cl. ....................................... 423/659; 62/55.5; 118/719; 118/724; 260/439 CY; 422/62; 422/129; 422/198; 422/202; 422/234; 423/593; 427/124; 427/250
[58] Field of Search ...................... 23/252 R; 62/55.5; 417/48; 423/659,593; 427/124, 250; 422/129, 198, 199, 234, 235, 202, 62

[56] References Cited

U.S. PATENT DOCUMENTS

| | | | |
|---|---|---|---|
| 2,408,721 | 10/1946 | Altsheler | 23/252 R |
| 2,684,287 | 7/1954 | Seavey | 23/252 R X |
| 3,252,652 | 5/1966 | Trendenburg et al. | 417/48 |
| 3,310,227 | 3/1967 | Milleron | 62/55.5 X |
| 3,485,054 | 12/1969 | Hogan | 62/55.5 |
| 3,579,998 | 5/1971 | Thibault et al. | 62/55.5 |
| 4,023,398 | 5/1977 | French et al. | 62/55.5 X |

OTHER PUBLICATIONS

D. Young et al., Vapor Synthesis: A New Technique in Synthetic Chemistry, J. Appl. Chem. Biotechnol., Vol. 25, p. 641-651, Feb. 5, 1976.

Primary Examiner—Joseph Scovronek
Attorney, Agent, or Firm—Young & Thompson

[57] ABSTRACT

Apparatus for the chemical synthesis of an evaporant and a liquid has a cryogenic pumping device between the evaporant source and the reaction region and a pump causes the liquid to be continuously recirculated until the reaction is completed, the pressure in the evaporation region being maintained substantially lower than that in the reaction region by differential pumping.

29 Claims, 5 Drawing Figures

CHEMICAL SYNTHESIS APPARATUS AND METHOD

This invention relates to chemical synthesis apparatus. It has particular, though not exclusive, application where metal or other vapours produced at high temperatures e.g. in the range 200°–4000° C. are used as reactants in formation of chemical products and on a batch or a continuous basis.

Applications are inter alia in the synthesis of organometallic sandwich compounds, mixed low-valence metal oxides, organic polymers which contain metal atoms, alloys, semi-conductor materials and ceramics, surface deposition of metal vapours on catalyst supports.

Examples of such synthesis occur in the cocondensation of the vapours of certain metals especially the transition metals of groups IV to VIII with organic compounds such as benzene, toluene and mesitylene. Many metal atom vapours act as catalyst precursors for the oligomerisation of organic compounds, (for example, butadiene), which is another type of application of the apparatus.

In accordance with conventional methods reactions are carried out within an enclosure at reduced pressure and there are two major problems which limit the applicability of the process as follows:

(i) A requirement for the furnace, within which one of the reactants e.g. a refractory metal, is vaporised to be maintained at a very low pressure in general means that the second reactant e.g. an organic ligand or solvent carrying such a ligand, must be maintained at a temperature low enough to reduce its vapour pressure to the required level, and at this low temperature the reaction rate can often be too low for reasonable yield.

(ii) The product formed in the reaction at these low temperatures in general freezes on to the walls of the reaction vessel thus forming an insulating layer as the reaction progresses and the product builds up on the walls of the reaction chamber; under these conditions radiation from the furnace and energy from the reaction may not be removed sufficiently rapidly from the system and thus the temperature of the reactant could rise and the requisite low vapour pressure would not be maintained. This sets a limit to the amount of material which may be synthesised in any one cycle.

With conventional chemical synthesis apparatus the vaporisation of these metals takes place from a furnace at high temperatures whereas the desired chemical reactions often take place at low temperatures either due to chemical considerations or due to the necessity of keeping the vapour pressure of the organic material sufficiently low so that the metal vapour furnace can still operate. Thus in certain instances to ensure reasonable yield in the reaction it is necessary for the reaction to take place at a temperature at which the vapour pressure of one or more of the components is in excess of that at which the high temperature furnace, for example an electron beam evaporation source, can be suitably operated. Vapour pressure in the region of the furnace mouth should not exceed $10^{-3}$ Torr, and in the case of an electron beam source it should be less than $10^{-4}$ Torr. Depending on the nature of the material producing the vapour with an unsuitable partial pressure, the operation of the furnace could be adversely affected. In the case, for example, of an electron beam source, reaction of said vapour with the electron emitter or filament could lead to premature degradation of said filament, and in the case of any furnace, pyrolysis of said vapour on the heated filaments could lead to breakdown of the vapour and contamination of the system, loss of electrical insulation etc.

Due to the comparative complexity of this type of synthesis apparatus close-down, removal of product, recharging and reinitiation of the reaction cycle is necessarily a time consuming operation and thus continuous operation would be desirable in production applications. However since the reaction vessel is a closed system and the product is in general in a frozen state it is not readily feasible to implement continuous operation with the concomitant requirements of continuous feed of reactant and removal of product.

It is an object of the present invention to provide a synthesis apparatus which overcomes the above problems.

In accordance with one aspect of the present invention, there is provided chemical synthesis apparatus comprising an evacuable chamber enclosing a reaction region, means mounting evaporation means for evaporating a first chemical constituent into said reaction region, differential pumping means arranged to maintain a pressure differential between the evaporation means and the reaction region, inlet means for introducing a second chemical constituent into the reaction region, and means for removing the second constituent after reaction with the first constituent and returning it to the reaction region for further reaction with the first constituent.

Thus, the use of differential pumping techniques enables the reactants to be maintained at temperatures where the vapour pressure is say two or three orders higher than that appertaining in the region of the furnace used for vaporising the second reactant material, and to enable the operation of the system to be continued over an extended period the surface of reactant presented to the metal vapour is continually renewed.

The reaction chamber coolant could be e.g. 'Cardice' with temperature −80° C., and a vapor pressure of $10^{-2}$ to $10^{-3}$ Torr could be maintained in the reaction vessel whilst the pressure in the furnace region is of the order of $10^{-5}$ Torr.

Chemical synthesis apparatus and method in accordance with the present invention, will now be described, by way of example, with reference to the accompanying drawings, in which.

Figures 1, 2:
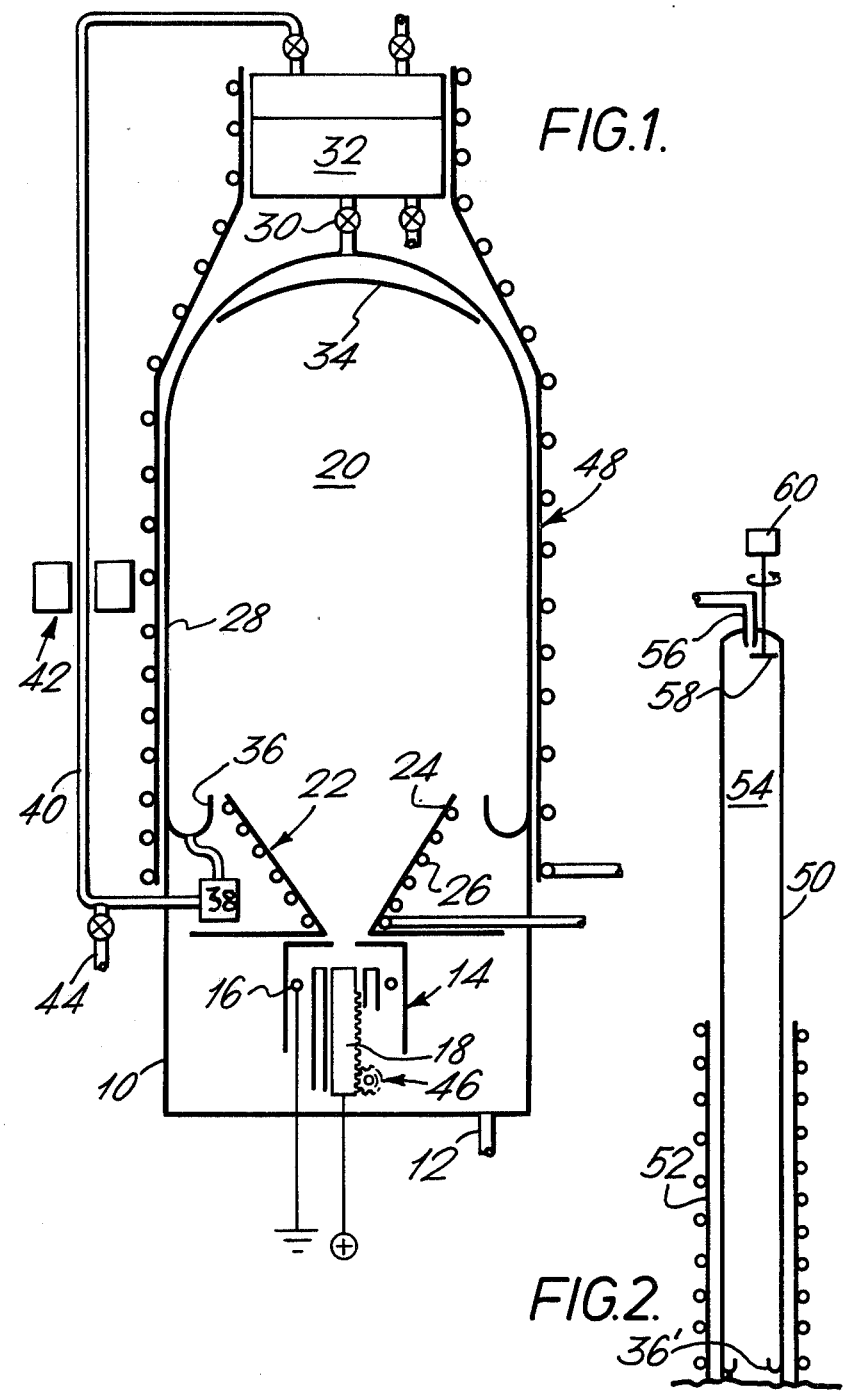
FIG. 1 is a schematic representation of one embodiment of the apparatus.
FIGS. 2 to 5 are schematic representations of parts of apparatus of other embodiments of the invention.

Referring to FIG. 1, an evacuable, substantially cylindrical container 10 is connected by a conduit 12 to conventional vacuum pumping equipment.

An electron beam vapour source 14 comprises a filament 16 and an evaporant rod electrode 18. Although usually the rod electrode of such a source is earthed, and the filament is at a high negative potential, it may be found desirable instead to earth the filament 16 and to apply a high positive potential to the rod 18. This polarity arrangement avoids attraction by other parts of the apparatus, which are also earthed, of electrons from the filament 16. Such undesirable attraction of electrons from the filament may adversely affect the synthesis.

It is envisaged, however, that the evaporation source of any embodiment of the apparatus may be a sputtering source, and especially a magnetron sputtering source.

In order to operate the electron beam evaporation source 14 efficiently, the pressure in the source region of the container 10 is required to be less than $10^{-4}$ Torr, whereas in order to achieve the desired temperature in the reaction region 20 at the upper part of the container 10, the pressure therein is required to be appreciably higher, say $\gtrsim 5 \times 10^{-3}$ Torr. To achieve this pressure differential, a cryogenic pumping device 22 is disposed between the source 14 and the reaction region 20. The device 22 comprises a hollow metal cone 24 that opens up away from the outlet of the source 14 towards the reaction region 20. The cone 24 is cooled by a flow of liquid nitrogen through a coiled pipe 26. Thus, the vapour from the source 14 passes through the cone 24 into the reaction region 20, where it tends to condense on the wall 28 of the container 10.

The liquid reactant is introduced at the top of the container 10 via an inlet pipe 30 from a reservoir 32. The reactant is directed on to a deflecting shield 34, which directs it to the upper part of the cylindrical wall 28. The reactant flows down the wall 28, reacting with the evaporant and into an annular collecting channel 36 around the inner circumference of the container 10 at the lower end of the wall 28. The liquid is drained from the channel 36, and is pumped by a pump 38 to a return pipe 40 which extends out through the wall 28 and back to the reservoir 32.

Although the return path 40 is shown being outside the container 10, this may, alternatively, extend within the container so as to redirect the partially-reacted liquid on to the container wall 28 at the top thereof. Alternatively, it is envisaged that the return pipe 40 may re-direct the partially-reacted liquid directly to the inlet pipe 30 without mixing with fresh reactant from the reservoir 32.

A continuous flow of the reactant is thus arranged between the reservoir 32, down the wall 28, where the reaction with the evaporant occurs, and back via the return pipe 40. As the reactant flows down the wall 28 usually only a portion of it combines with the evaporant from the source 14. The progress of the reaction is monitored, for example by a spectrophotometer 42, until the required degree of reaction is achieved.

At that time, the return to the reservoir 32 is closed and the reacted liquid drained via pipe 44.

It will be appreciated that the progress of the reaction can be monitored by other means, for example visual or other electro-optical means.

Since it is possible that the time for which the reactant from the reservoir 32 needs to be circulated through the reaction region 20 may exceed the lifetime of any evaporant charge on the hearth of the electron beam source 14, it is arranged to provide the charge, which comprises the rod 18, as a continuous feed, for example by a rack and pinion mechanism 46.

When one batch of reactant from the reservoir 32 has been reacted with the evaporant to the required degree, the flow through the inlet pipe 30 may be temporarily stopped while this reactant is drained and a fresh charge introduced into the reservoir 32.

The pump 38 is preferably mounted, as shown, within the container 10 so as to avoid having to feed vacuum pipes through the container wall. The pump may be a magnetically actuated pump.

The pressure within the reaction region 20 of the chamber 10 is maintained below $10^{-2}$ Torr by means of a refrigerated jacket 48 that extends over the wall 28 so as to enclose the collecting channel 36, and preferably also upwards so as to enclose the reservoir 32. The vacuum seal between the reaction region 20 and the source 14 may thus be somewhat separated from the jacket 48 to avoid problems associated with low temperature vacuum seals of the O-ring type.

FIG. 2 shows part of another embodiment of chemical synthesis apparatus, with only those parts being shown that differ materially from the apparatus as described with reference to FIG. 1.

The evacuable container 50 of FIG. 2 is an elongate cylinder with its length substantially greater than its diameter, and preferably, but not necessarily, more than 10 times the diameter. A refrigerated jacket 52 extends over the lower portion of the cylinder from the region of the collecting channel 36' upwards for preferably between one-third and one-half of the length of the chamber. The jacket 52 could, however, extend a shorter or a longer distance up the chamber from the channel 36'.

The reactant, or a solution of the reactant, is introduced into the reaction region 54 through a small capillary tube 56 at the closed top of the chamber 50. The liquid may be spread on to the chamber wall by any suitable means, and, as shown in FIG. 2 by way of example, this is done by directing the liquid from the tube 56 on to the edge of a disc 58. The disc 58 is rotatably mounted about a vertical axis, and is spun about this axis by means of a motor 60. The liquid is thus flung on to the inner wall of the chamber 50.

At the upper entrance region of the chamber 50 the pressure may be of the order of several tens of millimeters, but the pressure reduces as the refrigerated zone within the jacket 52 is approached. Thus, as the liquid flows down the wall of the chamber 50 the reaction occurs as previously described and the pressure within the evaporant source region (not shown) is maintained by suitable differential pumping means.

The temperature of a liquid film flowing through a reaction chamber of chemical synthesis apparatus in accordance with the present invention can be adjusted to the maximum value compatible with an acceptable vapour pressure within the apparatus by initially cooling the apparatus down to the required temperature, for example by passing liquid nitrogen through a cooling jacket, prior to adjusting the rate of flow of a refrigerant. This may be done by having liquid nitrogen gas boil off from its container such that the rate of removal of heat balances that of generation and radiation from the evaporant source, at the selected temperature for operation within the system.

Figure 3:
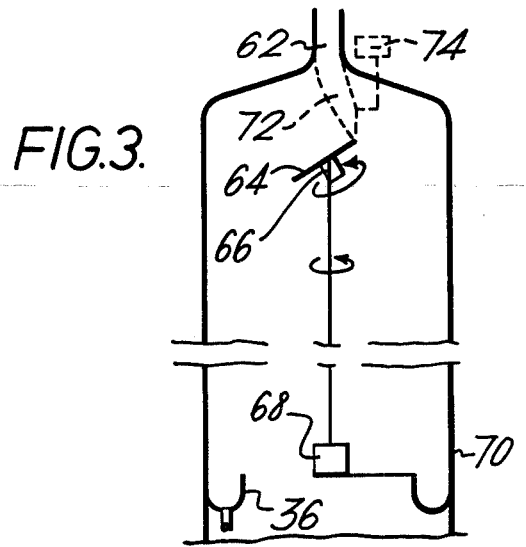

Reference will now be made to FIG. 3 which shows a different arrangement for depositing the incoming reactant on to the wall of the vacuum chamber.

The liquid reactant or a solution of the reactant is fed through a small tube 62 on to a rapidly rotating disc 64 which may be oriented at any angle, but preferably within the range of 30° to 60° to the horizontal. The reactant is ejected from the edge of the disc 64 by centrifugal action so as to cover a portion of the chamber wall. The disc 64 is rotated about its axis by a motor 66, and in addition to the rotary motion, the disc 64 is made to precess about a vertical axis by means of a further motor 68 which may conveniently drive and support the motor 66 from the lower end of the evacuable chamber 70, for example by being supported by the collecting channel 36.

In an alternative arrangement, if the reactant is fed directly on to the disc 64, this can conveniently be done by a flexible tube 72, shown in dashed outline in FIG. 3. In this arrangement, the precession of the disc 64 is preferably an oscillatory motion over an angle sufficient to give substantially 360° coverage of the wall of the container by the incoming liquid, whilst preventing entanglement of the feed tube 72, which is driven by a motor 74. Alternatively, the feed could be into a trough which may be rotated with the disc 64 about its vertical axis.

It will be appreciated that differential pumping means other than the single cooled cone 24 of FIG. 1 may also be employed.

Figure 4:
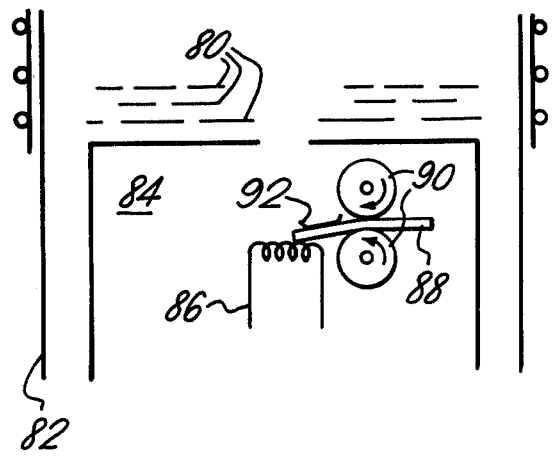

One alternative arrangement, shown in FIG. 4, comprises a plurality of apertured baffles 80 that extend across an evacuable container 82 so as to separate a source region 84 from the upper reaction region (not shown). The apertures in the diaphragms 80 open around the source 84 so as to present a larger pumping aperture to the reaction region than to the source region, so that the evaporation means can be maintained at a lower pressure than the reaction region.

FIG. 4 also shows, by way of example, an alternative evaporation means. This comprises a heated resistant element 86 on to which is continuously fed a wire or strip 88 that provides the evaporant source. The wire 88 is driven between a pair of rollers 90, and directed on to the element 86 by a deflector 92.

Figure 5:
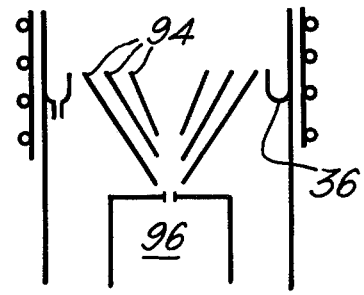

FIG. 5 depicts a still further embodiment of differential pumping means. The differential pumping is achieved by a plurality of hollow coaxial cones 94 of different angles. It is to be understood, however, that a single cone, or two or more coaxial cones, of the same angle may be employed. The cones 94 are mounted with their truncated apices directly over the outlet of the evaporation source 96, which may be of any suitable kind, so that the transit of high temperature vapour from the source 96 through the spaces between the cones 94 results in pumping of the evaporant into the reaction region above the collecting channel 36.

It will be appreciated that the reactant entering the top of the evacuable chamber in any embodiment of the apparatus may be in the form of a liquid, a solution, or a suspension of finely-divided solids in liquid.

According to one example of the method of the present invention, bis-cycloocta-1,5-diene iron, an organometallic compound, is synthesised in the following manner:

Iron metal placed on the hearth of an electron beam source is heated by bombardment with electrons emitted from a molybdenum filament provision having been made to prevent molybdenum contamination of the charge by obviating any direct optical path between filament and charge. Electron emission is produced by the application of a high voltage between the filament and hearth while the filament is heated by means of passage of an electric current. In this way vapour of iron atoms is produced and projected towards the reaction region where there is simultaneously introduced vapour, liquid or solutions in petroleum ether of cycloocta-diene. The walls of the chamber are cooled by a bath of solid carbon dioxide in acetone.

Pressure in the reaction region is above $10^{-3}$ Torr. Liquid nitrogen cooled metal hollow cones located coaxially above the hearth cryogenically pump the excess vapour of the cyclooctadiene thus reducing the amount entering the furnace region. Pumping apertures located in the base of the electron beam source are of larger area than the aperture between the source and the reaction region. The effect of these devices is to maintain the pressure within the electron beam source at about $10^{-4}$ Torr notwithstanding the higher pressure in the reaction region. The synthesised product bis-cycloocta-1,5-diene iron is extracted as a solution from the walls of the reaction vessel after allowing said walls to warm up to room temperature, or preferably, at reduced temperatures via the circulating system.

We claim:

1. Chemical synthesis apparatus comprising: a vacuum chamber enclosing a reaction region and an evaporation region; means for maintaining a vacuum in said chamber; evaporation means mounted in said evaporation region for producing a first chemical constituent; differential pumping means mounted in said chamber to separate said evaporation region from said reaction region, said differential pumping means, when said chamber is evacuated, maintaining residual gas pressure within said evaporation region at an appreciably lower pressure than within said reaction region and passing said evaporated first chemical constituent from said evaporation region into said reaction region; inlet means mounted on said chamber for introducing a second chemical constituent into said reaction region, and conduit means to remove the reacted first and second chemical constituents from said reaction region and to return said reacted constituents to said reaction region for reaction with a further quantity of said first constituent.

2. Apparatus according to claim 1, wherein said conduit means is arranged to conduct said reacted constituents to said inlet means for mixing with a further quantity of said second constituent.

3. Apparatus according to claim 1, comprising means arranged to analyse said reacted constituents to determine the progress of the reaction before said reacted constituents are returned to the reaction region.

4. Apparatus according to claim 3, wherein said analysing means is arranged to shut off flow of the second constituent to the reaction region when the reaction has progressed to a predetermined state.

5. Apparatus according to claim 1, wherein the conduit means comprises a channel member adjacent the inner circumference of the wall of said vacuum chamber.

6. Apparatus according to claim 1, wherein said conduit means passes out of the vacuum chamber before returning the reacted constituents to the reaction region.

7. Apparatus according to claim 1, wherein said conduit means includes a pump.

8. Apparatus according to claim 7, wherein the pump is a magnetically-operable pump.

9. Apparatus according to claim 7, wherein said pump is mounted within the vacuum chamber.

10. Apparatus according to claim 1 comprising a deflector member mounted in said chamber downstream of said inlet means such that said second constituent is arranged to impinge on said deflector member and is thereby directed towards the wall of the vacuum chamber.

11. Apparatus according to claim 10, wherein said vacuum chamber has an axis of symmetry, said first constituent is directed into the reaction region substantially along said axis, and the deflector member is inclined at an angle to said axis.

12. Apparatus according to claim 10, comprising means for rotating the deflector member about its axis thereby to spread said second chemical constituent evenly over said inner wall of said vacuum chamber.

13. Apparatus according to claim 11, comprising means for rotating the axis of rotation of the deflector member about said axis of the chamber, whereby said deflector member is arranged to precess beneath said inlet means.

14. Apparatus according to claim 13 wherein said axis rotating means is arranged to oscillate the deflector member in both directions about said axis of the chamber.

15. Apparatus according to claim 1, in which said evaporation means comprises a sputtering source.

16. Apparatus according to claim 15, in which the sputtering source is a magnetron sputtering source.

17. Apparatus according to claim 1, in which the differential pumping means comprises a cooled surface arranged above said evaporation means whereby the evaporant is arranged to pass over said surface before entering said reaction region.

18. Apparatus according to claim 1 in which cooling means is arranged around the said vacuum chamber to cool said reaction region thereof.

19. A method of chemical synthesis, comprising establishing an evaporation region and a reaction region within an evacuated chamber, establishing an evaporation source in said evaporation region, evaporating a first chemical constituent from said evaporation source in said evaporation region into said reaction region, introducing a second chemical constituent into said reaction region, maintaining the pressure within said evaporation region substantially lower than the pressure within said reaction region by differential pumping, removing said reacted first and second chemical constituents in admixture with unreacted second constituent from said reaction region and subsequently returning said removed constituents to said reaction region for reaction with a further quantity of said first constituent.

20. A method according to claim 19, wherein the removed constituents are mixed with a further quantity of said second constituent before being returned to the reaction region.

21. A method according to claim 19, wherein the removed constituents are analyzed before being returned to the reaction region to determine the degree of progress of the reaction.

22. A method according to claim 21, wherein the return of the removed constituents to the reaction region is stopped when the analysis indicates that the reaction has reached a predetermined state.

23. A method according to claim 19, wherein the second constituent is directed onto the wall towards the top of the vacuum chamber and is collected at the bottom of the wall.

24. A method according to claim 23, wherein the second constituent is directed onto a rotating surface within the vacuum chamber for deposition on the chamber wall by centrifugal force.

25. A method according to claim 24, wherein the axis of the rotating surface is rotated with respect to the chamber wall.

26. A method according to claim 25, wherein the rotating surface is oscillated with respect to the chamber wall.

27. A method according to claim 19, wherein the removed constituents are pumped back to the reaction region.

28. The method of claim 19, in which the differential pumping is produced by dividing said chamber into said evaporation and reaction regions by means defining at least one small aperture.

29. A method according to claim 28, wherein said means defining the aperture is cooled.

* * * * *